(12) United States Patent
O'Leary

(10) Patent No.: US 7,743,644 B2
(45) Date of Patent: *Jun. 29, 2010

(54) METHOD FOR DETERMINING DENSITY OF INSULATION

(75) Inventor: Robert J. O'Leary, Newark, OH (US)

(73) Assignee: Owens Corning Intellectual Capital, LL CDE (US)

( * ) Notice: Subject to any disclaimer, the term of this patent is extended or adjusted under 35 U.S.C. 154(b) by 343 days.

This patent is subject to a terminal disclaimer.

(21) Appl. No.: 11/599,872

(22) Filed: Nov. 15, 2006

(65) Prior Publication Data

US 2007/0214868 A1 Sep. 20, 2007
US 2010/0058836 A9 Mar. 11, 2010

Related U.S. Application Data

(63) Continuation-in-part of application No. 10/969,427, filed on Oct. 20, 2004, now abandoned, which is a continuation-in-part of application No. 10/689,770, filed on Oct. 21, 2003, now Pat. No. 6,928,859.

(51) Int. Cl.
*G01N 9/02* (2006.01)
(52) U.S. Cl. ..................................... 73/32 R
(58) Field of Classification Search ............... 73/32, 73/32 R
See application file for complete search history.

(56) References Cited

U.S. PATENT DOCUMENTS

| | | | |
|---|---|---|---|
| 2,755,660 A | 7/1956 | Kammermeyer et al. | |
| 2,912,851 A | 11/1959 | Karnes | |
| 3,524,342 A | 8/1970 | Hobbs | |
| 3,590,634 A | 7/1971 | Pasternak et al. | |

(Continued)

FOREIGN PATENT DOCUMENTS

GB 2 103 695 2/1983

(Continued)

OTHER PUBLICATIONS

Standard Test Methods for Thickness & Density of Blanket or Batt Thermal Insulations.

(Continued)

*Primary Examiner*—Hezron Williams
*Assistant Examiner*—Alex Devito
(74) *Attorney, Agent, or Firm*—James J. Dottavio; Jason S. Fokens

(57) ABSTRACT

An apparatus for determining the density of insulation in a cavity of a structure includes a sensor that is held in a substantially fixed position relative to the insulation for sensing the force of the insulation against the sensor. The force is used to determine the density of the insulation, which, in turn, is used to determine the thermal resistance or R-value of the insulation. The apparatus may include a fixture for supporting the sensor and holding the sensor in the substantially fixed position. A method for determining the density of loose-fill, blown-in-place insulation comprises the step of providing a structure with a cavity having a known depth. The cavity is filled with insulation. A sensor is held in a substantially fixed position relative to the insulation to measure force exerted on the sensor by the insulation. The measured force is used to determine the density of the insulation. The thermal resistance of the insulation is determined from the known cavity depth and insulation density.

11 Claims, 8 Drawing Sheets

U.S. PATENT DOCUMENTS

| | | | |
|---|---|---|---|
| 3,788,125 A | | 1/1974 | Kirchstein et al. |
| 3,808,876 A | | 5/1974 | Kershaw |
| 4,052,885 A | | 10/1977 | Shuck |
| 4,095,454 A | | 6/1978 | Fisher |
| 4,177,618 A | * | 12/1979 | Felter ............... 52/742.13 |
| 4,207,674 A | | 6/1980 | Heronema |
| 4,231,129 A | | 11/1980 | Winch |
| 4,311,037 A | | 1/1982 | Gotchel et al. |
| 4,337,666 A | | 7/1982 | Bhattacharyya et al. |
| 4,401,147 A | | 8/1983 | Beck et al. |
| 4,459,843 A | | 7/1984 | Durham |
| 4,506,542 A | | 3/1985 | Rose |
| 4,515,007 A | | 5/1985 | Herman |
| 4,603,618 A | | 8/1986 | Soltis |
| 4,649,738 A | | 3/1987 | Waldie et al. |
| 4,676,091 A | | 6/1987 | Schuster et al. |
| 4,679,423 A | | 7/1987 | Ballentine |
| 4,712,347 A | * | 12/1987 | Sperber ............... 52/404.1 |
| 4,815,316 A | | 3/1989 | Tantram |
| 4,854,011 A | | 8/1989 | Staheli et al. |
| 4,869,197 A | | 9/1989 | Gupta et al. |
| 4,911,021 A | | 3/1990 | Shortridge |
| 4,979,390 A | | 12/1990 | Schupack et al. |
| 5,005,403 A | | 4/1991 | Steudle et al. |
| 5,036,601 A | | 8/1991 | Mulle, Jr. et al. |
| 5,051,452 A | | 9/1991 | Romesberg |
| 5,060,398 A | | 10/1991 | Wolens |
| 5,157,960 A | | 10/1992 | Brehm et al. |
| 5,192,348 A | | 3/1993 | Ludwig |
| 5,209,402 A | | 5/1993 | DeBra et al. |
| 5,287,674 A | | 2/1994 | Sperber |
| 5,353,630 A | | 10/1994 | Soda et al. |
| 5,355,653 A | | 10/1994 | Henri |
| 5,373,727 A | | 12/1994 | Heller et al. |
| 5,417,101 A | | 5/1995 | Weich |
| 5,445,704 A | | 8/1995 | Dizon |
| 5,445,792 A | | 8/1995 | Rickloff et al. |
| 5,456,104 A | | 10/1995 | Rosen |
| 5,485,754 A | | 1/1996 | Harpster |
| 5,505,091 A | | 4/1996 | Ali |
| 5,509,295 A | | 4/1996 | Bartoli |
| 5,513,515 A | | 5/1996 | Mayer |
| 5,594,161 A | | 1/1997 | Randhahn et al. |
| 5,595,602 A | | 1/1997 | Harlan |
| 5,633,453 A | | 5/1997 | Johnson |
| 5,641,368 A | | 6/1997 | Romes et al. |
| 5,698,772 A | | 12/1997 | Deruyter et al. |
| 5,913,546 A | | 6/1999 | Kuchenbrod et al. |
| 6,047,518 A | * | 4/2000 | Lytle ............... 52/742.13 |
| 6,119,506 A | | 9/2000 | Gibson et al. |
| 6,330,779 B1 | | 12/2001 | Kinzler |
| 6,450,009 B1 | | 9/2002 | Hartikainen et al. |
| 6,463,791 B1 | | 10/2002 | Berube et al. |
| 6,521,086 B2 | | 2/2003 | Smith, Jr. |
| 6,568,282 B1 | | 5/2003 | Ganzi |
| 6,581,451 B2 | | 6/2003 | Ence et al. |
| 6,591,661 B2 | | 7/2003 | Davey |
| 6,817,941 B1 | | 11/2004 | Gatov |
| 6,820,819 B2 | | 11/2004 | Sperber |
| 6,826,920 B2 | | 12/2004 | Wacker |
| 6,928,859 B2 | * | 8/2005 | O'Leary et al. ............. 73/32 R |
| 7,055,370 B2 | | 6/2006 | Tinianov et al. |
| 7,055,371 B2 | | 6/2006 | Babineau, Jr. et al. |
| 7,059,173 B2 | | 6/2006 | Babineau, Jr. et al. |
| 7,404,260 B2 | | 7/2008 | Felinger et al. |
| 2003/0217588 A1 | | 11/2003 | Jalbert et al. |
| 2005/0268697 A1 | * | 12/2005 | Babineau et al. ............. 73/32 R |
| 2007/0006664 A1 | | 1/2007 | Suda et al. |
| 2007/0113650 A1 | | 5/2007 | Fellinger et al. |

OTHER PUBLICATIONS

Standard Handbook for Mechanical Engineers, Seventh Edition, pp. 14-74-14-75.

* cited by examiner

METHOD FOR DETERMINING DENSITY OF INSULATION

RELATED APPLICATIONS

This application is a continuation-in-part of U.S. patent application Ser. No. 10/969,427, filed Oct. 20, 2004, now abandoned entitled Apparatus and Method for Determining Density of Insulation which is a continuation-in-part of U.S. patent application Ser. No. 10/689,770, filed Oct. 21, 2003 which has issued as U.S. Pat. No. 6,928,859.

TECHNICAL FIELD AND INDUSTRIAL APPLICABILITY OF THE INVENTION

This invention relates in general to an apparatus and method for determining the density of insulation, and in particular, to an apparatus and method for determining the density of a loose-fill, blown-in-place fibrous insulation.

BACKGROUND OF INVENTION

In recent years, a greater emphasis has been placed on the use of insulation materials in dwellings or other structures to promote energy conservation and noise reduction. At the same time, innovative architectural designs have created a variety of shapes and sizes that do not always lend themselves to the use of a conventional fibrous batting, which is often available in rolls of uniform width. The conventional fibrous batting often fails to fully fill the space in which the batting is used. This has created a need for a technique for applying fibrous insulation that does not use uniform width batting.

This need has been fulfilled to a limited extent by developing various blown-in-place insulation techniques, wherein loose-fill fibrous insulation is blown into a cavity between the framing members of the wall, ceiling, or floor of a dwelling. The loose-fill insulation is capable of completely filling the cavity, regardless of its shape and size, thus effectively achieving a uniform volume of insulation for optimum energy conservation, as well as sound insulation purposes.

While blown-in-place insulation techniques have addressed insufficient fill problems inherent with insulation batting, one of the advantages of batting lost to blown-in-place insulation is the batting's ability to maintain insulation quality. This includes, of course, the density and thickness of the fibrous insulation, which is important to achieve a uniform thermal resistance. The thermal resistance of the insulation batting is often associated with a given "R-value". When insulation batting is purchased, for example, to place in a new dwelling, it is often purchased by specifying a desired R-value. If installed in accordance with minimal prescribed installing techniques, the purchaser, due to uniform dimensions of insulation batting, can be count on at the insulation value having a certain thermal resistance.

When a blown-in-place insulation technique is employed, the advantage of controlling R-value associated with batting is lost. As a consequence, it is often necessary to also employ a technique for determining the density of the blown-in-place insulation for assuring that the insulation has the desired R-value.

Various techniques have been employed for the determining density in blown-in-place fibrous insulations. In one technique, a known mass of loose-fill is blown into a cavity. The volume of the filled cavity is measured. The mass is divided by the cavity volume to get density. A problem with this technique is that it slows down the installation process of the insulation and therefore, is not used. Moreover, it is difficult to calculate the actual volume of insulation that is blown into the cavity because there are so many features (i.e., windows, doors, devices, etc.) in the area that take up volume.

In another known technique, a space is first filled with blown-in-place insulation. Then, a sample of insulation of a known volume is removed from a wall cavity and weighed. Since the volume of the sample is known, it is possible to determine the density (i.e., weight per volume) of the insulation in the cavity. The R-value of the insulation may then be determined in a known manner simply by knowing the thickness of the insulation in the cavity. In some instances, the quantity of insulation may be loose or compressed. As a consequence, error in determining the density of the insulation can be magnified if care is not taken to correctly remove the sample or average a number of samples. This is also a very time consuming technique and consequently is often not practiced by insulation installers.

In view of the above techniques, it is apparent that there exists a need in the art for an improved apparatus and method for installing insulation that is blown into open wall cavities to a prescribed density wherein the improved apparatus and method provide increased accuracy.

SUMMARY OF INVENTION

The above objects, as well as other objects not specifically enumerated, are achieved by an apparatus for determining the density of insulation in a cavity of a dwelling or other structure. The apparatus is in the form of a sensor that is held in a substantially fixed position within the cavity of the structure and relative to the insulation in the cavity for sensing the force of the insulation against the sensor. The force is used to determine the density of the insulation, which, in turn, is used to determine the thermal resistance or R-value of the insulation.

An alternative apparatus includes a sensor and a fixture supporting the sensor. The fixture is structured and dimensioned to hold the sensor in a substantially fixed position relative to the insulation within the cavity.

A method for determining the density of loose-fill, blown-in-place insulation comprises the initial step of providing a structure that includes framing members and a sheath forming at least one cavity having a known depth. A sensor is held in a substantially fixed position relative to the insulation in the cavity. Then, force exerted on the sensor by the insulation is measured. The measured force is used to determine the density of the insulation. The thermal resistance of the insulation is determined from the known cavity depth and insulation density.

Various objects and advantages of this invention will become apparent to those skilled in the art from the following detailed description of the preferred embodiment, when read in light of the accompanying drawings.

DETAILED DESCRIPTION

Figure 1:
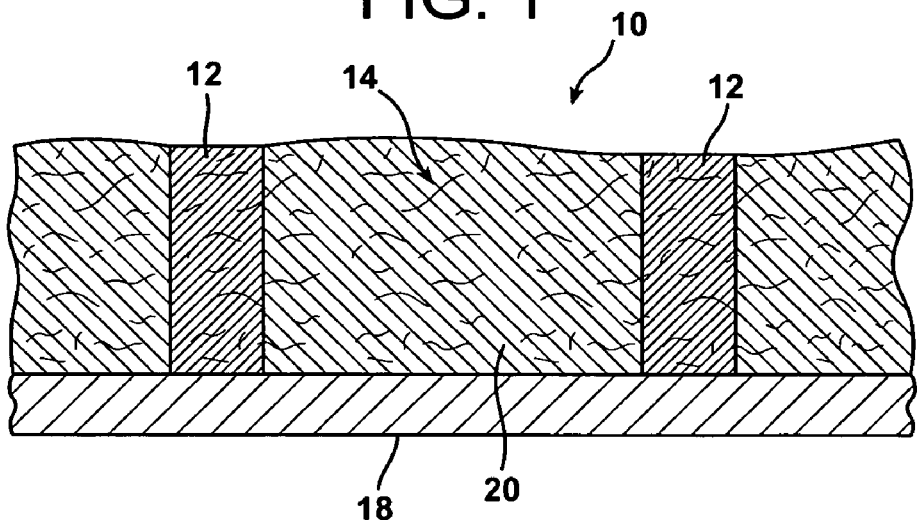
FIG. 1 is a diagrammatic representation in plan of a partial structure of a dwelling or other structure.

Referring now to the drawings, there is illustrated in FIG. 1 a partial structure of a dwelling or other structure, indicated generally at 10, including framing members 12, such as wall studs, ceiling joists, or floor joists. Various other framing members, not shown, the purpose of which will be apparent to those skilled in the art, maybe included in the structure 10. A cavity 14 is formed between the framing members 12. An outer side of the cavity 14 is covered with an exterior sheathing 18, which sheathes the structure 10 except at locations of doors and windows, not shown.

Insulation 20 is installed in the cavity 14 to prevent heat passage either outwardly or inwardly through the structure, and to minimize sound transmission therethrough. The insulation 20 is preferably a loose-fill, blown-in-place fibrous insulation. The insulation 20 may consist of any suitable material useful for insulation purposes. Such insulation 20 may be installed in a conventional manner, such as through use of a blower apparatus, not shown, which picks up the insulation in an air stream and carries the insulation to the cavity 14 through a tube or hose, also not shown. As shown in FIGS. 1, 3A, and 4-9, the loose-fill, blown-in-place fibrous insulation 20 maintains its position within the cavity 14 in the absence of netting and without the use of external structures, mechanisms or devices.

Figure 2:
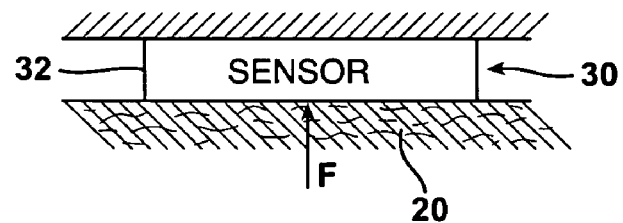
FIG. 2 is a schematic representation in plan of an apparatus for determining the density of a loose-fill, blown-in-place fibrous insulation in a cavity of the structure illustrated in FIG. 1.

An apparatus for determining the density of insulation 20 in the cavity 14 is schematically represented at 30 in FIG. 2. The determination of density leads to the determination of thermal resistance, or the R-value, of the insulation 20. The apparatus 30 comprises a sensor 32 that is adapted to be held in a substantially fixed position relative to the insulation 20 in the cavity 14. The term "substantially" with respect to the term "fixed" means that the sensor 32 will be held in a position relative to the insulation in a manner that allows reliable density determinations to be repeatedly made by the sensor 32. That is to say, the sensor 32 may suffer some minor deviation in position as long as the density determinations remain reliable.

According to the present invention, the sensor 32 senses force F, or a change in force, which is used to determine density, as will be described in greater detail in the description herein below. Numerous embodiments of the apparatus 30 can be used to carry out the invention. Some examples of such embodiments are set forth in the following paragraphs.

Figure 3A:
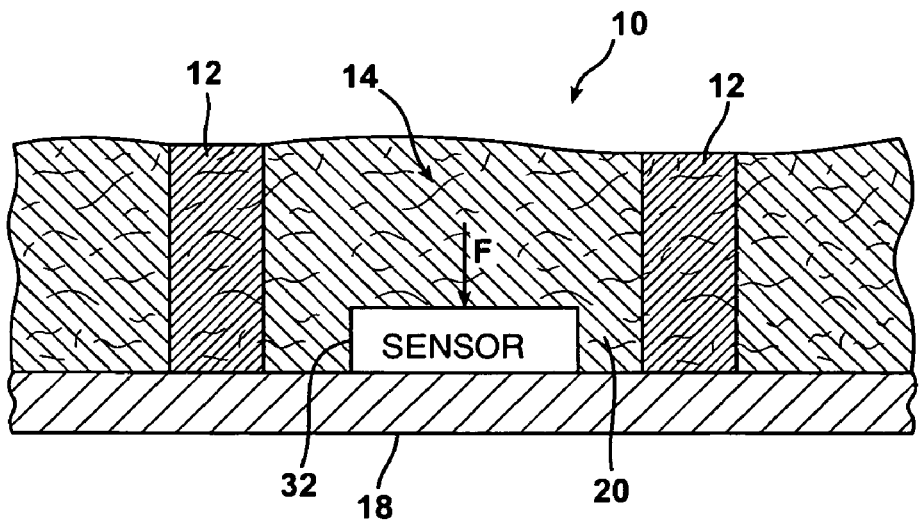
FIGS. 3A and 3B are diagrammatic representations in plan of sensors of the apparatus according to the invention supported within the cavity of the structure illustrated in FIG. 1.
Figure 3B:
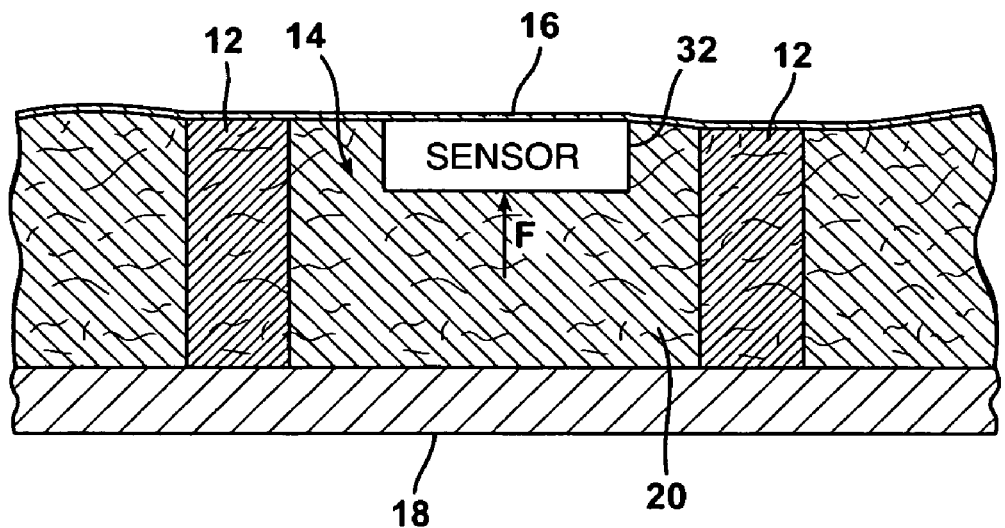

In one embodiment of the invention, the sensor 32 is supported within the cavity 14. This may be accomplished by attaching the sensors to the sheathing 18 as shown in FIG. 3A. When the insulation 20 is blown into the cavity 14, the sensor 32 senses the force F of the insulation. In accordance with this embodiment, a measurement of force F may be taken from within the cavity 14 via a physical or wireless connection, not shown, by the sensor 32. Optionally, as shown in FIG. 3B, the sensor may be placed against netting 16. Although FIG. 3B shows a netting 16, the structure of FIGS. 1, 3A, and 4-9 indicates the insulation is maintained in the cavity 14 in the absence of netting or other external structures, mechanisms or devices.

Figure 4:
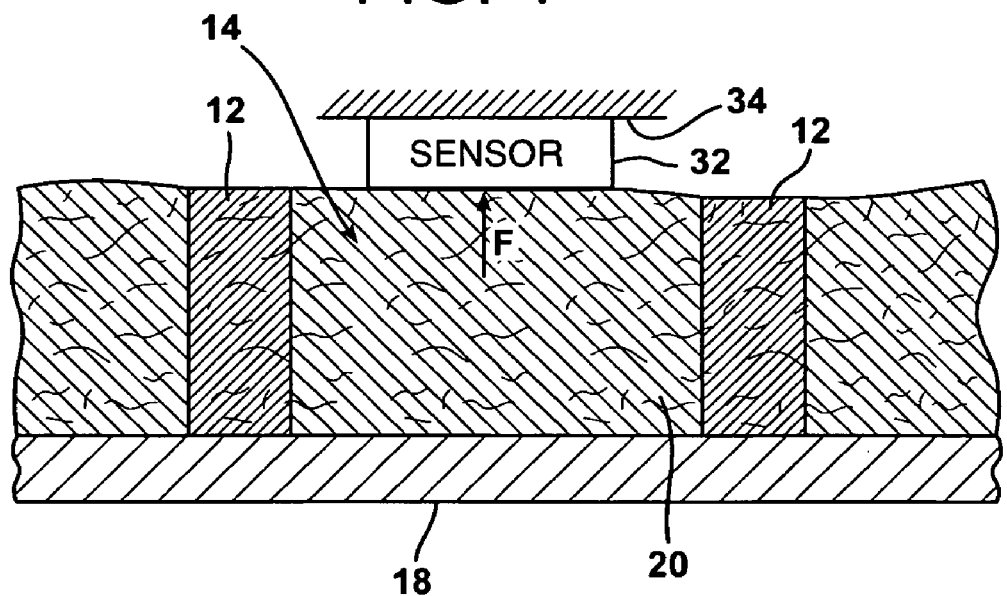
FIG. 4 is a schematic representation in plan of a fixture for supporting a sensor outside the cavity, according to the invention.

In another embodiment of the invention, the sensor 32 is supported against the insulation 20 but is located outside the cavity 14. This can be accomplished in any suitable manner. For example, a fixture 34 could be provided for supporting the sensor 32, as schematically illustrated in FIG. 4. The fixture 34 can be any suitable structure that is adapted to hold the sensor 32 in a substantially fixed position relative to the insulation 20.

Figure 5:
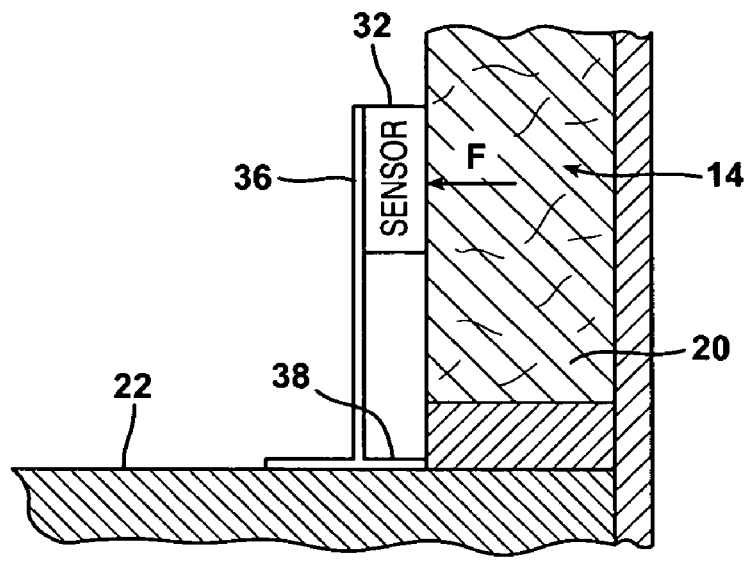
FIG. 5 is a diagrammatic representation in plan of a fixture according to one embodiment of the invention.

In FIG. 5, there is illustrated a fixture in the form of a standard 36 that may be supported by a supporting surface 22 adjacent the cavity 14 with the insulation 20 therein. The sensor 32 is adapted to be supported by the standard 36 in a manner so that the sensor 32 can be repeatedly held in a fixed position relative to the insulation 20. For example, the standard 36 may include a foot 38 for establishing a set distance for the standard 36 away from the insulation 20.

Figure 6:
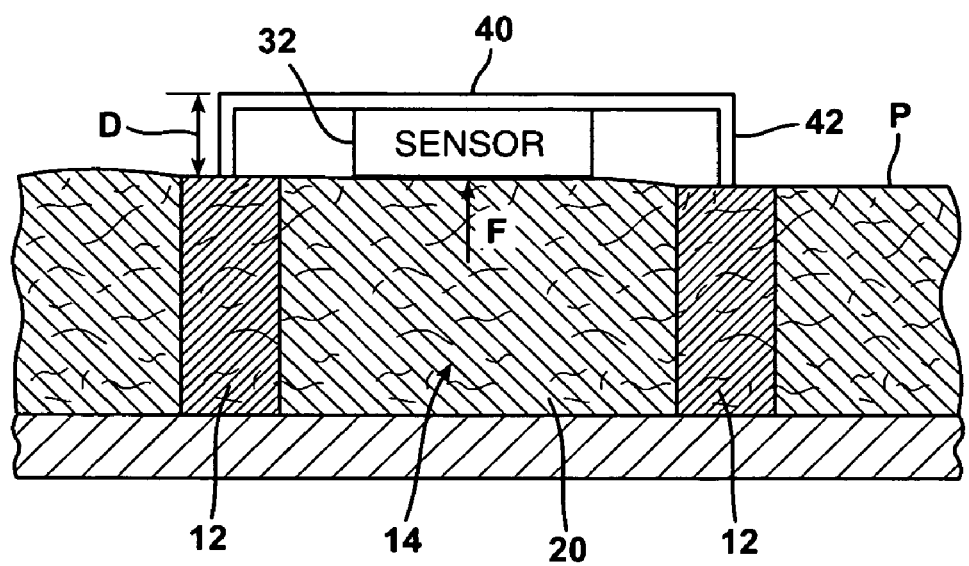
FIG. 6 is a diagrammatic representation in plan of a fixture according to another embodiment of the invention.

In FIG. 6, there is illustrated a fixture in the form of a plate 40 that is adapted to be repeatedly held in a fixed position relative to the insulation 20. The plate 40 can be held in contact with the insulation 20, or, as shown in FIG. 6, spaced from the insulation 20, as long as the position is substantially consistent to permit correlated determinations of density to be made. In the illustrated embodiment, the plate 40 is adapted to be held a fixed distance D from the insulation 20 in the cavity 14 with each determination of density made by the apparatus. This can be accomplished with legs 42 that extend from the plate 40 to engage the framing members 12, although such is not required. The distance D is preferably a distance whereby the sensor 32 does not extend beyond a plane P that is coplanar with the inner sides of the framing members 12, or into the cavity 14 between the framing members 12.

Figure 7:
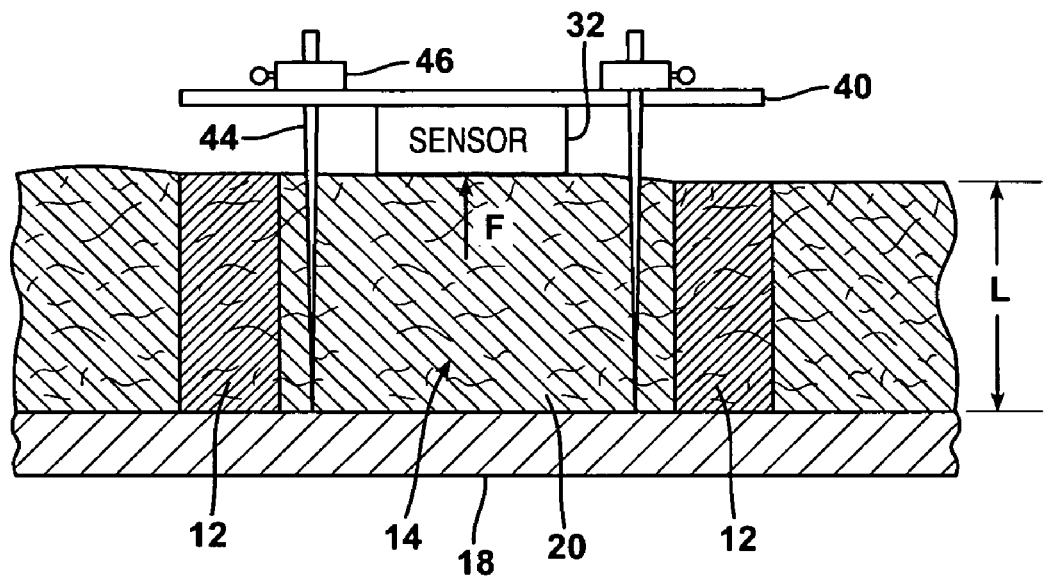
FIG. 7 is a diagrammatic representation in plan of a fixture according to yet another embodiment of the invention.

In FIG. 7, there is illustrated another fixture, which is also in the form of a plate 40. Extending from the plate 40 are pins 44 that are adapted to pass through the insulation 20 in the cavity 14 without substantially affecting its density, and engage the inner side of the sheath 18. The length L of the pins 44 may be fixed or adjustable to accommodate framing members 12 having different dimensions. For example, the length L of the pins 44 may be approximately 3-½ inches in length if the framing members 12 are nominal 2×4 studs or approximately 5-½ inches in length if the framing members 12 are nominal 2×6 ceiling joists. Adjustment of the pins 44 may be accomplished in any suitable manner, such as, for example, providing apertures, not shown, through the plate 40 and a clamp 46 in fixed position relative to the plate 40 and in alignment with the apertures. The pins 44 may pass through the apertures and the clamps 46 may secure the pins 44 in a desired position relative to the plate 40. Alternatively, the pins 44 may be telescopically adjustable, or adjustable in some other suitable manner.

The sensor 32 according to one embodiment of the invention may be in the form of a load cell for measuring the force of the insulation 20 in the cavity 14. Such a sensor 32 would be suitable for use within or outside the cavity 14, as schematically represented in FIGS. 2 and 4, or in any of the embodiments of the invention described herein. Any conventional load cell may be suitable for carrying out the invention.

Figure 8:
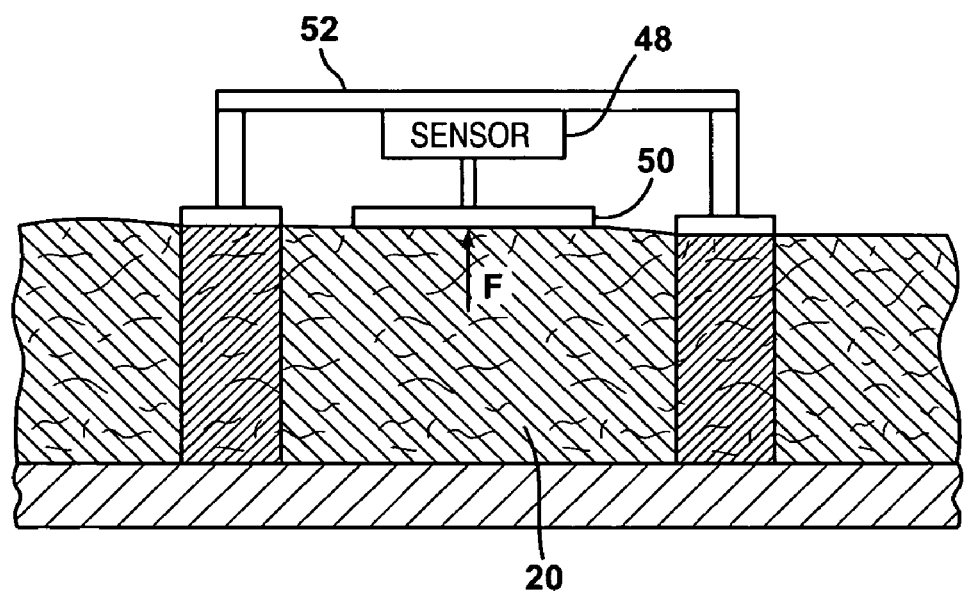
FIG. 8 is a diagrammatic representation in plan of a sensor according to one embodiment of the invention.

In FIG. 8, there is illustrated a sensor in the form of a force transducer 48. The force transducer 48 is adapted to measure the force F encountered by a contact plate 50 held against the insulation 20. The force transducer 48 may be a digital transducer or an analog transducer. The force transducer 48 can be held in a fixed relation to the insulation 20 in any suitable, such as with the use of any of the fixture 52 shown, or any of the fixtures described above. Alternatively, an analog spring-force meter may be used in the place of the force transducer 48. In accordance with the invention, the insulation 20 will exert a force F against the force transducer 48, and that force F will be directly related to the density of the insulation 20.

Figure 9:
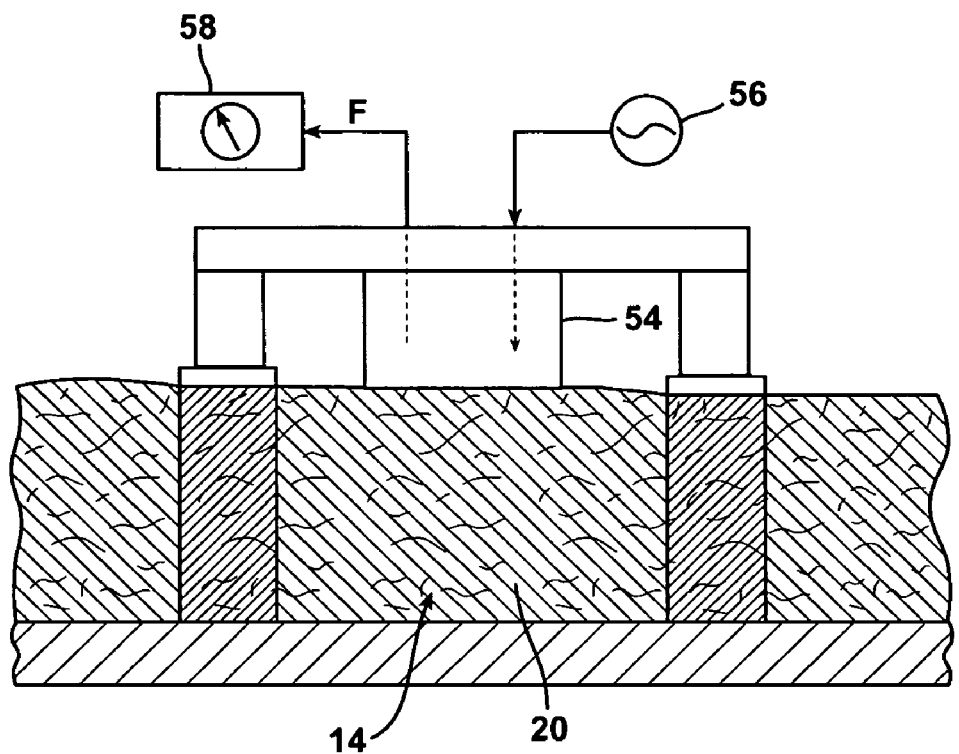
FIG. 9 is a diagrammatic representation in plan of a sensor according to another embodiment of the invention.

In FIG. 9, there is illustrated another sensor in the form of an air cup 54. The air cup 54 is adapted to press against the insulation 20 in the cavity 14. Air, at a given pressure, is introduced into the air cup 54 from a source 56. The air pressure, or a pressure drop, in the air cup 54 can be measured via a gauge 58. The pressure in the air cup 54 will be directly related to the density of the insulation 20. The source 56 may either blow air into the air cup 54 or, in the alternative; the source 56 may draw air into the air cup 54. [PLEASE PROVIDE MORE DETAILED DESCRIPTION HERE IF POSSIBLE]

Figure 10:
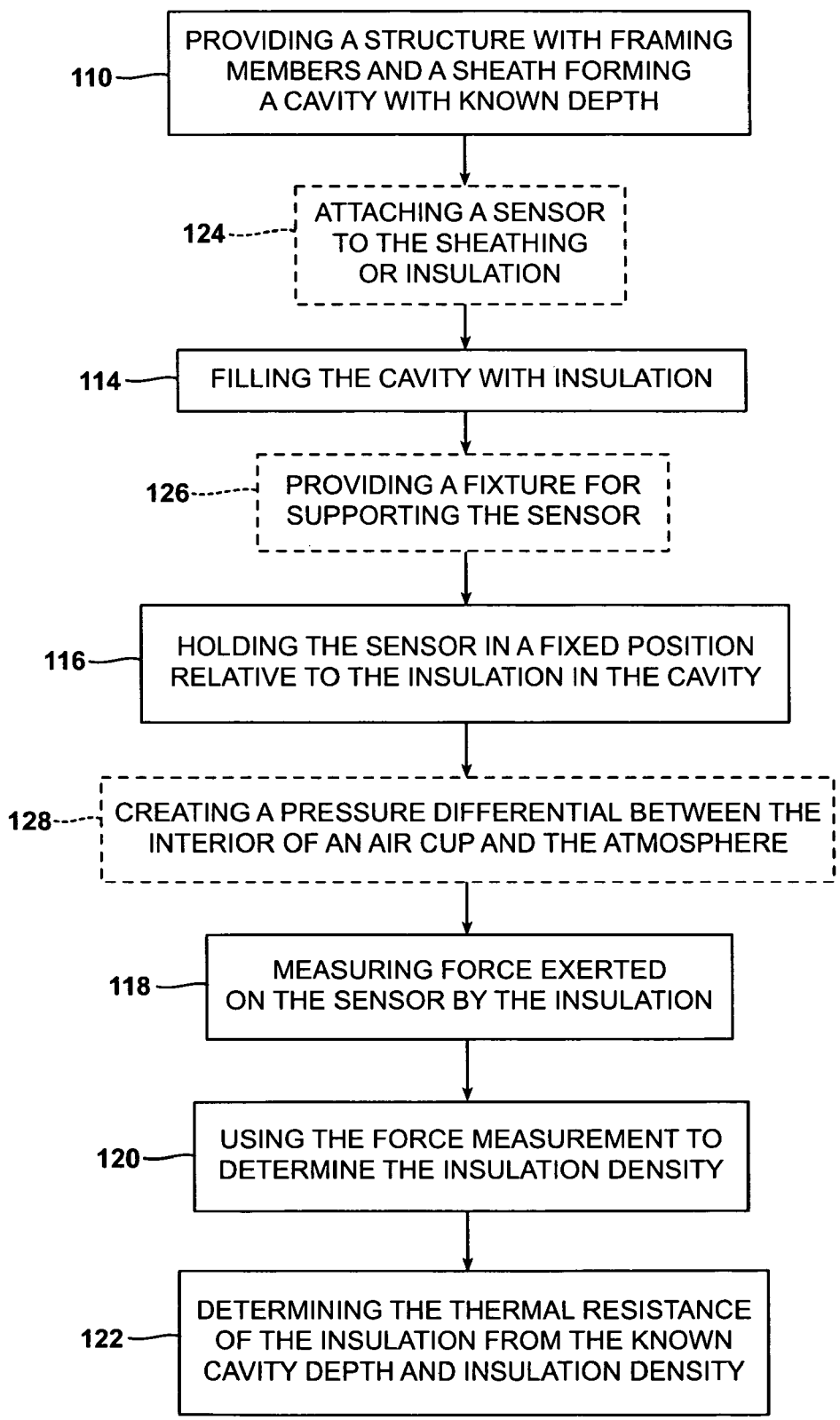
FIG. 10 is a block diagram of a method for determining the density of a loose-fill, blown-in-place fibrous insulation.

In FIG. 10 there is illustrated a method for determining the density of loose-fill, blown-in-place insulation in a cavity defined between framing members of a dwelling or other structure. A method according to a preferred embodiment of the invention may comprise an initial step 110 of providing a structure having framing members and a sheath forming at least one cavity having a known depth of thickness. In step 114, the cavity is filled with insulation. The insulation is preferably a loose-fill, blown-in-place fibrous insulation.

In a subsequent step 116, a sensor is held in a substantially fixed position relative to the insulation in the cavity. In step 118, the sensor measures force exerted on the sensor by the insulation. In step 120, the force is used to determine the density of the insulation. In step 122, the thermal resistance of the insulation is determined from the known cavity depth and insulation density.

In optional step 124, the sensor is supported within the cavity. The sensor may be attached to the sheathing prior to filling the cavity with the insulation. When the insulation is blown into the cavity, the sensor senses the force exerted against the sensor by the insulation.

In an alternative step 126, a fixture is provided for supporting the sensor outside the cavity and holding the sensor in a substantially fixed position relative to the insulation. The fixture may be in the form of a standard supported by a supporting surface adjacent the cavity and the insulation therein. Alternatively, the fixture may be in the form of a plate that holds the sensor against the insulation. The plate could be held a distance from the framing members by legs that engage the framing members. Alternatively, the plate could be held a distance from the sheathing by pins that pass through the insulation and engage the sheathing. The pins could be adjusted in length to accommodate framing members having different dimensions.

The sensor of step 116 may be in the form of a load cell that senses the force of the insulation against the sensor. Alternatively, the sensor may be a digital or analog force transducer. The transducer can be held in a fixed position relative to the insulation with the fixture provided in step 126. A spring-force meter may be used in the place of the transducer. Alternatively, the sensor may be in the form of an air cup that is pressed against the insulation. It will be appreciated that if the sensor provided in step 116 is an air cup, then an optional step 128 may be performed in which air is introduced into the air cup at a given source pressure. In step 118, the force exerted is then determined by measuring the air pressure in the air cup, such as by using a gauge. The pressure in the air cup is directly related to the density of the insulation.

Figure 11:
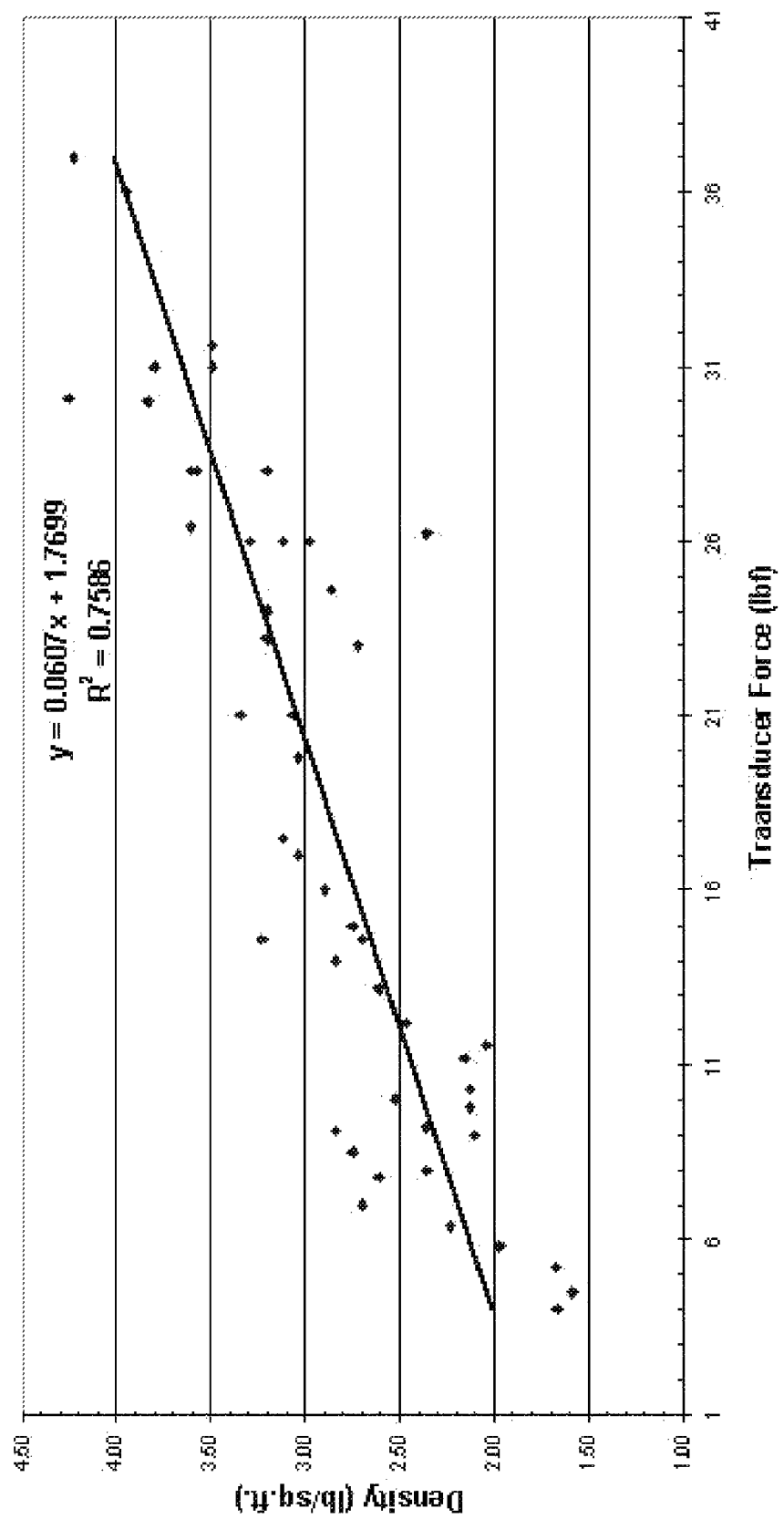
FIG. 11 is graph of empirical data relating to the relationship between the density and the spring force of the loose-fill insulation and a polynomial used in a regression to arrive at the empirical data.

The aforementioned force transducer 48 and spring-force meter rely on the natural spring force of the loose-fill insulation to gage density. As the density of loose-fill insulation increases, the spring force increases proportionally. Using polynomial regression, an empirical relationship can be found between the density and the spring force of the loose-fill insulation. An example of a polynomial and empirical data relating to the relationship between the density and the spring force for is shown in FIG. 11.

Figure 12:
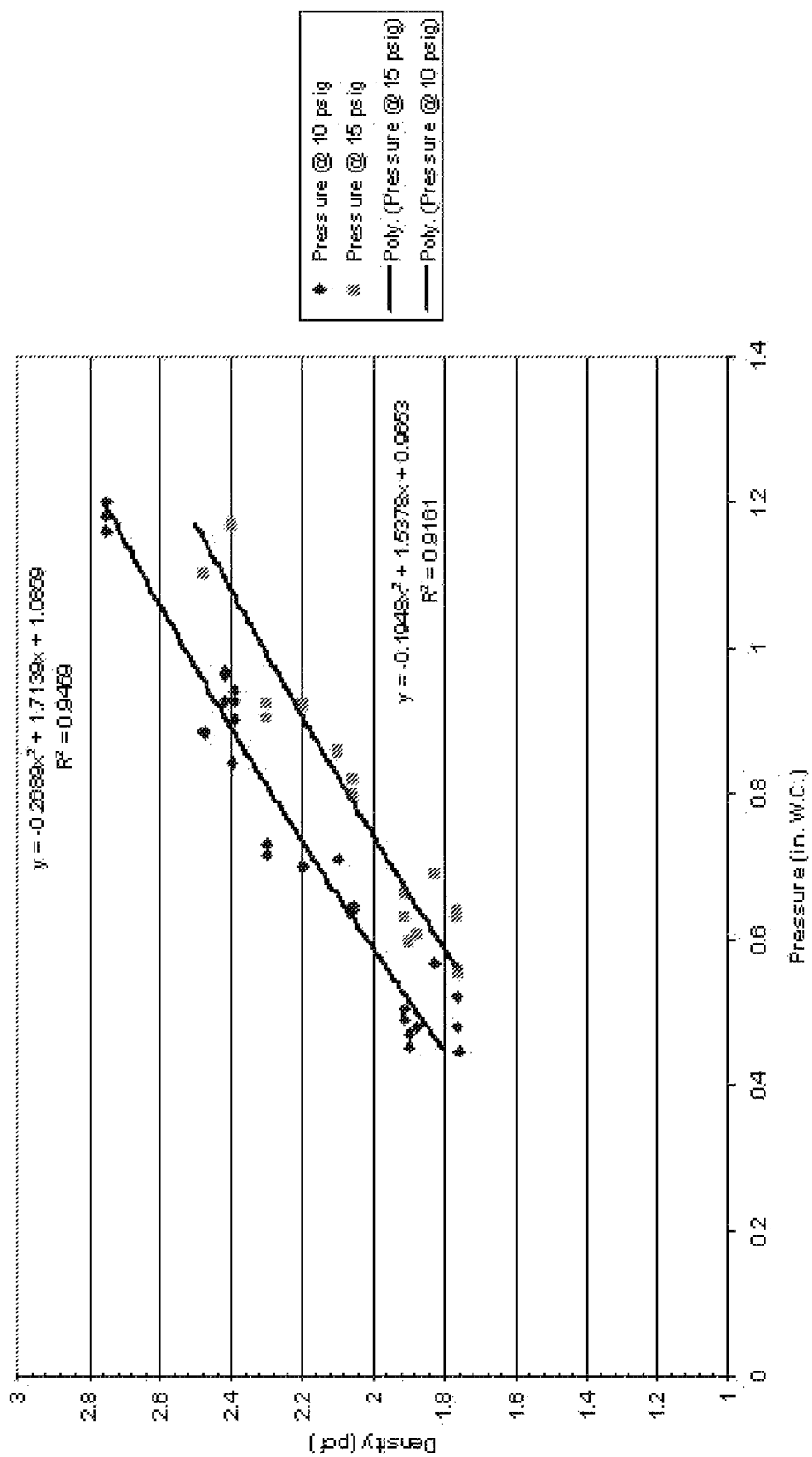
FIG. 12 is graph of empirical data relating to the relationship between the density and the pressure drop through the loose-fill insulation and a polynomial used in a regression to arrive at the empirical data.

The embodiment of the apparatus or method that uses the air cup relies on the natural resistance to flow of the loose-fill insulation to create a pressure drop. For a given source pressure, the loose-fill insulation has a characteristic pressure drop for a given density. Further, back pressure created on the high-pressure side of the loose-fill insulation is directly proportional to density. Using polynomial regression, an empirical relationship can be found between the density and pressure drop. An example of a polynomial and empirical data relating to the relationship between the density and the pressure drop through the insulation is shown in FIG. 12.

Factors that can affect either embodiment of the invention include the morphology, diameter, characteristic length, and shape of the fibers of the insulation factors, the binder content, if a binder is used, and other factors that are not mentioned.

The loose-fill thermal conductance, which is inversely proportionate to thermal resistance, can be related to the density by laboratory testing. The data can then curve fitted, as shown in FIGS. 11, and 12.

The principle and mode of operation of this invention have been explained and illustrated in its preferred embodiment. However, it must be understood that this invention may be practiced otherwise than as specifically explained and illustrated without departing from its spirit or scope.

What is claimed is:

1. A method for determining the density of loose-fill, blown-in-place insulation in a cavity defined between framing members of a structure, the method comprising the steps of:
   (a) providing a structure including framing members and a sheath forming at least one cavity having a known depth;
   (b) filling the cavity with insulation;
   (c) holding a sensor within the cavity in a substantially fixed position relative to the insulation in the cavity;
   (d) measuring force exerted on the sensor by the insulation;
   (e) using the force to determine the density of the insulation; and
   (f) determining the thermal resistance of the insulation from the known cavity depth and insulation density.

2. The method of claim 1, wherein said framing members are wall studs.

3. The method of claim 1, wherein said framing members are ceiling joists.

4. The method of claim 1, wherein said framing members are floor joists.

5. A method for determining the density of loose-fill, blown-in-place insulation in a cavity defined between framing members of a structure, the method comprising the steps of:

(a) providing a structure including framing members and a sheath forming at least one cavity having a known depth;
(b) filling the cavity with insulation;
(c) providing a fixture for supporting a sensor positioned outside the cavity, wherein the fixture is in the form of a plate that supports the sensor against the insulation;
(d) holding the sensor in a substantially fixed position relative to the insulation in the cavity;
(e) measuring force exerted on the sensor by the insulation;
(f) using the force to determine the density of the insulation; and
(g) determining the thermal resistance of the insulation from the known cavity depth and insulation density.

6. The method of claim 5, wherein the sensor is a force transducer.

7. The apparatus of claim 5, wherein the sensor is in the form of a spring-force meter.

8. A method for determining the density of loose-fill, blown-in-place insulation in a cavity defined between framing members of a structure, the method comprising the steps of:
(a) providing a structure including framing members and a sheath forming at least one cavity having a known depth;
(b) filling the cavity with insulation;
(c) providing a sensor in a substantially fixed position relative to the insulation in the cavity, wherein the sensor is an air cup that is pressed against the insulation;
(d) introducing air into the air cup from a source, with the air being supplied at a given source pressure;
(e) measuring air pressure in the air cup, the air pressure being directly related to the density of the insulation;
(f) using the measured air pressure to determine the density of the insulation; and
(g) determining the thermal resistance of the insulation from the known cavity depth and insulation density.

9. A method for determining the density of loose-fill, blown-in-place insulation in a cavity defined between framing members of a structure, the method comprising the steps of:
(a) providing a structure including framing members and a sheath forming at least one cavity having a known depth;
(b) filling the cavity with insulation;
(c) providing a sensor in a substantially fixed position relative to the insulation in the cavity, wherein the sensor is an air cup that is pressed against the insulation;
(d) blowing air into the air cup at a given source pressure;
(e) measuring air pressure in the air cup, the air pressure being directly related to the density of the insulation;
(f) using the measured air pressure to determine the density of the insulation; and
(g) determining the thermal resistance of the insulation from the known cavity depth and insulation density.

10. A method for determining the density of loose-fill, blown-in-place insulation in a cavity defined between framing members of a structure, the method comprising the steps of:
(a) providing a structure including framing members and a sheath forming at least one cavity having a known depth;
(b) filling the cavity with insulation;
(c) providing a sensor in a substantially fixed position relative to the insulation in the cavity, wherein the sensor is an air cup that is pressed against the insulation;
(d) drawing air into the air cup at a given source pressure;
(e) measuring air pressure in the air cup, the air pressure being directly related to the density of the insulation;
(f) using the measured air pressure to determine the density of the insulation; and
(g) determining the thermal resistance of the insulation from the known cavity depth and insulation density.

11. A method for determining the density of loose-fill, blown-in-place insulation in a cavity defined between framing members of a structure, the loose-fill insulation including an adhesive, the method comprising the steps of:
(a) providing a structure including framing members and a sheath forming at least one cavity having a known depth;
(b) filling the cavity with insulation;
(c) providing a sensor in a substantially fixed position relative to the insulation in the cavity, wherein the sensor is an air cup that is pressed against the insulation;
(d) blowing air into the air cup at a given source pressure;
(e) measuring air pressure in the air cup, the air pressure being directly related to the density of the insulation;
(f) using the measured air pressure to determine the density of the insulation; and
(g) determining the thermal resistance of the insulation from the known cavity depth and insulation density.

* * * * *